(12) United States Patent
Mash, Jr. et al.

(10) Patent No.: US 9,415,110 B1
(45) Date of Patent: Aug. 16, 2016

(54) METHOD AND COMPOSITIONS FOR TARGETED DRUG DELIVERY TO THE LOWER GI TRACT

(71) Applicant: THE ARIZONA BOARD OF REGENTS ON BEHALF OF THE UNIVERSITY OF ARIZONA, Tucson, AZ (US)

(72) Inventors: Eugene A. Mash, Jr., Tucson, AZ (US); Pawel R. Kiela, Tucson, AZ (US); Fayez K. Ghishan, Tucson, AZ (US)

(73) Assignee: The Arizona Board of Regents on behalf of the Univeristy of Arizona, Tucson, AZ (US)

(*) Notice: Subject to any disclaimer, the term of this patent is extended or adjusted under 35 U.S.C. 154(b) by 0 days.

(21) Appl. No.: 14/271,251

(22) Filed: May 6, 2014

Related U.S. Application Data

(60) Provisional application No. 61/821,166, filed on May 8, 2013.

(51) Int. Cl.
 *C07H 15/26* (2006.01)
 *A61K 47/48* (2006.01)

(52) U.S. Cl.
 CPC ..... *A61K 47/48061* (2013.01); *A61K 47/48023* (2013.01); *C07H 15/26* (2013.01)

(58) Field of Classification Search
 CPC .............................................. A61K 47/48061
 See application file for complete search history.

(56) References Cited

U.S. PATENT DOCUMENTS

| | | | |
|---|---|---|---|
| 5,368,840 A | 11/1994 | Unger | 424/9 |
| 5,407,657 A | 4/1995 | Unger et al. | 424/9 |
| 5,458,127 A | 10/1995 | Unger et al. | 128/653.4 |
| 5,624,661 A | 4/1997 | Unger | 424/9.35 |
| 5,645,816 A | 7/1997 | Unger | 424/9.34 |
| 5,658,550 A | 8/1997 | Unger | 424/9.36 |
| 5,681,542 A | 10/1997 | Unger | 424/9.3 |
| 5,985,244 A | 11/1999 | Unger | 424/9.3 |
| 6,963,769 B1 | 11/2005 | Balaban et al. | 600/420 |
| 7,048,907 B2 | 5/2006 | Groman et al. | 424/9.2 |

(Continued)

FOREIGN PATENT DOCUMENTS

| | | | |
|---|---|---|---|
| EP | 2025350 | 2/2009 | A61K 49/06 |
| WO | WO9111175 | 8/1991 | A61K 9/22 |

(Continued)

OTHER PUBLICATIONS

Navath et al.; "Design, Synthesis, and Testing of a Molecular Truck for Colonic Delivery of 5-Aminosalicylic Acid"; Aug. 1, 2012; ACS Medicinal Chemistry Letters; 3: 710-714.*

(Continued)

*Primary Examiner* — Timothy Thomas
(74) *Attorney, Agent, or Firm* — Don D. Cha; Hamilton DeSanctis & Cha, LLP

(57) ABSTRACT

A composition and method for targeted delivery of substances to the lower GI tract comprises a base or scaffold carrier to which a drug or prodrug is fixed or covalently attached. Compound, when taken orally travels through the GI tract of a patient to the lower GI where bacterial azo reductace enzymes cleave the bonds, releasing the drug or prodrug from the base or scaffold carrier permitting the delivery of the drug to the vicinity of a target cell type in the GI tract. The base or scaffold, which remains as a by-product passes out of the GI tract in the feces.

7 Claims, 5 Drawing Sheets

(56) References Cited

U.S. PATENT DOCUMENTS

| | | | |
|---|---|---|---|
| 7,330,748 B2 | 2/2008 | Balaban et al. | 600/420 |
| 2003/0059368 A1 | 3/2003 | Groman et al. | 424/1.11 |
| 2005/0059881 A1 | 3/2005 | Balaban et al. | 600/420 |
| 2005/0181038 A1 | 8/2005 | Haas et al. | 424/450 |
| 2007/0009441 A1 | 1/2007 | Erathodiyil et al. | 424/9.34 |
| 2008/0167549 A1 | 7/2008 | Balaban et al. | 600/420 |
| 2010/0178243 A1 | 7/2010 | Haas et al. | 424/1.21 |
| 2010/0183504 A1 | 7/2010 | Chen | 424/1.29 |
| 2010/0255087 A1 | 10/2010 | Coulter | 424/457 |
| 2011/0104052 A1 | 5/2011 | Barnett et al. | 424/1.21 |
| 2014/0194428 A1* | 7/2014 | Abushakra et al. | 514/242 |

FOREIGN PATENT DOCUMENTS

| | | | |
|---|---|---|---|
| WO | WO9306148 | 4/1993 | C08G 63/20 |
| WO | WO9408509 | 4/1994 | A61B 5/055 |
| WO | WO9632967 | 10/1996 | A61K 49/00 |
| WO | WO0066180 | 11/2000 | A61K 49/00 |
| WO | WO02062397 | 8/2002 | A61K 51/00 |
| WO | WO02087632 | 11/2002 | A61K 51/00 |
| WO | WO2004002455 | 1/2004 | A61K 9/127 |
| WO | WO2005065724 | 7/2005 | A61K 49/00 |
| WO | WO2006010083 | 1/2006 | A61K 9/14 |
| WO | WO2009027690 | 3/2009 | C07K 14/47 |
| WO | WO2009045579 | 4/2009 | C12M 3/00 |
| WO | WO2009073193 | 6/2009 | B65B 35/56 |
| WO | WO2011035140 | 3/2011 | A61K 49/00 |
| WO | WO2011044545 | 4/2011 | A61K 47/42 |

OTHER PUBLICATIONS

Lai et al.; "Degradability of the Linear Azo Polymer Conjugated 5,5'-Azodisalicylic Acid Segment in the Main Chain for Colon-Specific Drug Delivery"; 2008; Journal of Applied Polymer Science; 108: 3305-3312.*

Rao et al.; "A sucrose-derived scaffold for multimerization of bioactive peptides"; 2011; Bioorganic & Medicinal Chemistry; 19: 6474-6482.*

Griffiths et al.; Slow Release 5-Aminosalicylic acid Therapy in Children with Small Intestinal Crohn's Disease; 1993; Journal of Pediatric Gastroenterology and Nutrition; 17:186-192.*

Rachmilewitz; "Coated mesalazine (5-aminosalicylic acid) versus sulphasalazine in the treatment of active ulcerative colitis: a randomized trial"; 1989; Br. Med. J.; 298:82-6.*

Deng M, Griffith JF, Zhu XM, Poon WS, Ahuja AT, Wang YX. Effect of ovariectomy on contrast agent diffusion into lumbar intervertebral disc: a dynamic contrast-enhanced MRI study in female rats. Magn Reson Imaging. Mar. 27, 2012. [Epub ahead of print] PubMed PMID: 22459440. (NPL #1).

Tan M, Burden-Gulley SM, Li W, Wu X, Lindner D, Brady-Kalnay SM, Gulani V, Lu ZR. MR Molecular Imaging of Prostate Cancer with a Peptide-Targeted Contrast Agent in a Mouse Orthotopic Prostate Cancer Model. Pharm Res. Apr. 2012;29(4):953-60. Epub Dec. 3, 2011. PubMed PMID: 22139536. (NPL #2).

Chesnick IE, Fowler CB, Mason JT, Potter K. Novel mineral contrast agent for magnetic resonance studies of bone implants grown on a chick chorioallantoic membrane. Magn Reson Imaging. Nov. 2011;29(9):1244-54. Epub Sep. 14, 2011. PubMed PMID: 21920685. (NPL #3).

De Naeyer D, Debergh I, De Deene Y, Ceelen WP, Segers P, Verdonck P. First order correction for T(2)*-relaxation in determining contrast agent concentration from spoiled gradient echo pulse sequence signal intensity. J Magn Reson Imaging. Jul. 18, 2011. doi: 10.1002/jmri.22681. [Epub ahead of print] PubMed PMID: 21769976. (NPL #4).

Shan L. Poly(ethylene glycol)-b-poly(L-lysine)-gadolinium-1,4,7,10-tetraazacyclododecane-1,4,7,10-tetra acetic acid micelle. May 31, 2011 [updated Jun. 23, 2011]. Molecular Imaging and Contrast Agent Database (MICAD) [Internet]. Bethesda (MD): National Center for Biotechnology Information (US); 2004-2011. Available from http://www.ncbi.nlm.nih.gov/books/NBK56207/PubMed PMID: 21735590. (NPL #5).

Shan L. Polyion complex micelles of poly(ethylene glycol)-b-poly(L-lysine)-gadolinium-1,4,7,10-tetraazacyclododecane-1,4,7,10-tetra acetic acid-dextran sulfate. May 31, 2011 [updated Jun. 23, 2011]. Molecular Imaging and Contrast Agent Database (MICAD) [Internet]. Bethesda (MD): National Center for Biotechnology Information (US); 2004-2011. Available from http://www.ncbi.nlm.nih.gov/books/NBK56202/PubMed PMID: 21735585. (NPL #6).

Shan L. Gadolinium-tetraazacyclododecane tetraacetic acid coupled with folate via bis(aminoethyl)ethylene glycol linker. Mar. 12, 2011[updated Apr. 19, 2011]. Molecular Imaging and Contrast Agent Database (MICAD) [Internet]. Bethesda (MD): National Center for Biotechnology Information (US); 2004-2011. Available from http://www.ncbi.nlm.nih.gov/books/NBK54071/PubMed PMID: 21542552. (NPL #7).

Keliris A, Ziegler T, Mishra R, Pohmann R, Sauer MG, Ugurbil K, Engelmann J. Synthesis and characterization of a cell-permeable bimodal contrast agent targeting β-galactosidase. Bioorg Med Chem. Apr. 15, 2011;19(8):2529-40. Epub Mar. 13, 2011. PubMed PMID: 21459584. (NPL #8).

Makino A, Harada H, Okada T, Kimura H, Amano H, Saji H, Hiraoka M, Kimura S. Effective encapsulation of a new cationic gadolinium chelate into apoferritin and its evaluation as an MRI contrast agent. Nanomedicine. Oct. 2011;7(5):638-46. Epub Feb. 17, 2011. PubMed PMID: 21333752. (NPL #9).

Tachibana Y, Enmi J, Mahara A, Iida H, Yamaoka T. Design and characterization of a polymeric MRI contrast agent based on PVA for in vivo living-cell tracking. Contrast Media Mol Imaging. Nov.-Dec. 2010;5(6):309-17. PubMed PMID: 21190268. (NPL #10).

Ishiguchi T, Takahashi S. Safety of gadoterate meglumine (Gd-DOTA) as a contrast agent for magnetic resonance imaging: results of a post-marketing surveillance study in Japan. Drugs R D. 2010;10(3):133-45. doi: 10.2165/11539140-000000000-00000. PubMed PMID: 20945944. (NPL #11).

Leung K. Gd-DOTA-c(Cys-Arg-Gly-Asp-Cys). Jun. 27, 2010 [updated Sep. 3, 2010]. Molecular Imaging and Contrast Agent Database (MICAD) [Internet]. Bethesda (MD): National Center for Biotechnology Information (US); 2004-2010. Available from http://www.ncbi.nlm.nih.gov/books/NBK45635/PubMed PMID: 20827824. (NPL #12).

Kalber TL, Kamaly N, So PW, Pugh JA, Bunch J, McLeod CW, Jorgensen MR, Miller AD, Bell JD. A low molecular weight folate receptor targeted contrast agent for magnetic resonance tumor imaging. Mol Imaging Biol. Aug. 2011; 13(4):653-62. PubMed PMID: 20809208. (NPL #13).

Bazeli R, Coutard M, Duport BD, Lancelot E, Corot C, Laissy JP, Letourneur D, Michel JB, Serfaty JM. In vivo evaluation of a new magnetic resonance imaging contrast agent (P947) to target matrix metalloproteinases in expanding experimental abdominal aortic aneurysms. Invest Radiol. Oct. 2010;45(10):662-8. PubMed PMID: 20733508. (NPL #14).

Leung K. Gadolinium-Tetraazacyclododecane-N',N'',N''',N''''-tetraacetic acid-Cys-Asn-Asn-Ser-Lys-Ser-His-Thr-Cys. Oct. 29, 2009 [updated Mar. 18, 2010]. Molecular Imaging and Contrast Agent Database (MICAD) [Internet]. Bethesda (MD): National Center for Biotechnology Information (US); 2004-2010. Available from http://www.ncbi.nlm.nih.gov/books/NBK26743/ PubMed PMID: 20641976. (NPL #15).

Zhang H. Gadolinium-1,4,7,10-tetraazacyclododecane-N',N',N',N'''-tetraacetic-monoamide-24-ca scade-polymer. Oct. 17, 2007 [updated Dec. 4, 2007]. Molecular Imaging and Contrast Agent Database (MICAD) [Internet]. Bethesda (MD): National Center for Biotechnology Information (US); 2004-2010. Available from http://www.ncbi.nlm.nih.gov/books/NBK23581/PubMed PMID: 20641779. (NPL #16).

Leung K. Gadolinium-1,4,7,10-tetraazacyclododecane-N',N'',N''',N''''-tetraacetic acid-Pro-Leu-Ala-Leu-Lys-Arg-Asp-Arg . Jun. 15, 2008 [updated Jul. 15, 2008]. Molecular Imaging and Contrast Agent Database (MICAD) [Internet]. Bethesda (MD): National Center for Biotechnology Information (US); 2004-2010. Available from http://www.ncbi.nlm.nih.gov/books/NBK23571/ PubMed PMID: 20641769. (NPL #17).

(56) References Cited

OTHER PUBLICATIONS

Zhang H. Gadolinium 1-((11-S)-3,10-diaza-13-carboxamido-11-carboxy-2,9-dioxotridecyl)-N,N',N"-tris(carboxymethyl-1,4,7,10-tetraazacyclododecane . Nov. 20, 2007 [updated Jan. 3, 2008]. Molecular Imaging and Contrast Agent Database (MICAD) [Internet]. Bethesda (MD): National Center for Biotechnology Information (US); 2004-2010. Available from http://www.ncbi.nlm.nih.gov/books/NBK23562/PubMed PMID: 20641760. (NPL #18).
Zhang H. Eu-chelate anti-fibrin antibody-conjugated perfluorocarbon nanoparticles . Jan. 17, 2008 [updated Feb. 20, 2008]. Molecular Imaging and Contrast Agent Database (MICAD) [Internet]. Bethesda (MD): National Center for Biotechnology Information (US); 2004-2010. Available from http://www.ncbi.nlm.nih.gov/books/NBK23285/PubMed PMID: 20641487. (NPL #19).
Zhang H. (Gd-chelate)2-Phe-His-Cys-Pro(OH)-Tyr(2-Cl)-Asp-Leu-Cys-His-Ile-Leu-(Gd-chelate)2 . Nov. 15, 2007 [updated Jan. 8, 2008]. Molecular Imaging and Contrast Agent Database (MICAD) [Internet]. Bethesda (MD): National Center for Biotechnology Information (US); 2004-2010. Available from http://www.ncbi.nlm.nih.gov/books/NBK23257/PubMed PMID: 20641459. (NPL #20).
Zhang H. Tri-gadolinium nitride PEGylated-hydroxylated endohedral metallofullerene . Oct. 28, 2008 [updated Dec. 1, 2008]. Molecular Imaging and Contrast Agent Database (MICAD) [Internet]. Bethesda (MD): National Center for Biotechnology Information (US); 2004-2010. Available from http://www.ncbi.nlm.nih.gov/books/NBK23240/PubMed PMID: 20641442. (NPL #21).
Zhang H. Gd-DOTA-anti-Aβ42-F(ab')2-antibody fragment (putrescine)n . Nov. 7, 2008 [updated Dec. 22, 2008]. Molecular Imaging and Contrast Agent Database (MICAD) [Internet]. Bethesda (MD): National Center for Biotechnology Information (US); 2004-2010. Available from http://www.ncbi.nlm.nih.gov/books/NBK23074/PubMed PMID: 20641279. (NPL #22).
Leung K. Dimeric Gd-tetraazacyclododecanetetraacetic acid-folate. Jan. 17, 2009 [updated May 3, 2009]. Molecular Imaging and Contrast Agent Database (MICAD) [Internet]. Bethesda (MD): National Center for Biotechnology Information (US); 2004-2010. Available from http://www.ncbi.nlm.nih.gov/books/NBK22997/PubMed PMID: 20641205. (NPL #23).
Zhang H. Gd-DOTA-G-NH(CH2)11CO-RSPAYYTAA-(CH2CH2O)8-R . Dec. 22, 2008 [updated Jan. 14, 2009]. Molecular Imaging and Contrast Agent Database (MICAD) [Internet]. Bethesda (MD): National Center for Biotechnology Information (US); 2004-2010. Available from http://www.ncbi.nlm.nih.gov/books/NBK22996/PubMed PMID: 20641204. (NPL #24).
Schühle DT, van Rijn P, Laurent S, Vander Elst L, Muller RN, Stuart MC, Schatz J, Peters JA. Liposomes with conjugates of a calix[4]arene and a Gd-DOTA derivative on the outside surface; an efficient potential contrast agent for MRI. Chem Commun (Camb). Jun. 28, 2010;46(24):4399-401. Epub May 13, 2010. PubMed PMID: 20467663. (NPL #25).
Kamaly N, Kalber T, Kenny G, Bell J, Jorgensen M, Miller A. A novel bimodal lipidic contrast agent for cellular labelling and tumour MRI. Org Biomol Chem. Jan. 7, 2010;8(1):201-11. Epub Nov. 5, 2009. PubMed PMID: 20024151. (NPL #26).
Künnemeyer J, Terborg L, Nowak S, Brauckmann C, Telgmann L, Albert A, Tokmak F, Kramer BK, Gansel A, Wiesmaller GA, Karst U. Quantification and excretion kinetics of a magnetic resonance imaging contrast agent by capillary electrophoresis-mass spectrometry. Electrophoresis. May 2009;30(10):1766-73. PubMed PMID: 19441033. (NPL #27).
Cosentino U, Pitea D, Moro G, Saracino GA, Villa A. Conformational behaviour determines the low-relaxivity state of a conditional MRI contrast agent. Phys Chem Chem Phys. May 28, 2009;11(20):3943-50. Epub Apr. 20, 2009. PubMed PMID: 19440623. (NPL #28).
Jastrzebska B, Lebel R, Therriault H, McIntyre Jo, Escher E, Guerin B, Paquette B, Neugebauer WA, Lepage M. New enzyme-activated solubility-switchable contrast agent for magnetic resonance imaging: from synthesis to in vivo imaging. J Med Chem. Mar. 26, 2009;52(6):1576-81. PubMed PMID: 19228016. (NPL #29).

Alsaid H, De Souza G, Bourdillon MC, Chaubet F, Sulaiman A, Desbleds-Mansard C, Chaabane L, Zahir C, Lancelot E, Rousseaux O, Corot C, Douek P, Briguet A, Letourneur D, Canet-Soulas E. Biomimetic MRI contrast agent for imaging of inflammation in atherosclerotic plaque of ApoE-/-mice: a pilot study. Invest Radiol. Mar. 2009;44(3):151-8. PubMed PMID: 19169144. (NPL #30).
Peldschus K, Hamdorf M, Robert P, Port M, Graessner J, Adam G, Herborn CU. Contrast-enhanced magnetic resonance angiography: evaluation of the high relaxivity low diffusible gadolinium-based contrast agent P846 in comparison with gadoterate meglumine in rabbits at 1.5 Tesla and 3.0 Tesla. Invest Radiol. Dec. 2008;43(12):837-42. PubMed PMID: 19002055. (NPL #31).
Park JA, Lee JJ, Jung JC, Yu DY, Oh C, Ha S, Kim TJ, Chang Y. Gd-DOTA conjugate of RGD as a potential tumor-targeting MRI contrast agent. Chembiochem. Nov. 24, 2008;9(17):2811-3. PubMed PMID: 18956393. (NPL #32).
Jacquier A, Bucknor M, Do L, Robert P, Corot C, Higgins CB, Saeed M. P846, a new gadolinium based low diffusion magnetic resonance contrast agent, in characterizing occlusive infarcts, reperfused ischemic myocardium and reperfused infarcts in rats. MAGMA. May 2008;21(3):207-18. Epub Apr. 30, 2008. PubMed PMID: 18446394. (NPL #33).
Lahrech H, Perles-Barbacaru AT, Aous S, Le Bas JF, Debouzy JC, Gadelle A, Fries PH. Cerebral blood volume quantification in a C6 tumor model using gadolinium per (3,6-anhydro) alpha-cyclodextrin as a new magnetic resonance imaging preclinical contrast agent. J Cereb Blood Flow Metab. May 2008;28(5):1017-29. Epub Jan. 9, 2008. PubMed PMID: 18183033. (NPL #34).
Chaubet F, Bertholon I, Serfaty JM, Bazeli R, Alsaid H, Jandrot-Perrus M, Zahir C, Even P, Bachelet L, Touat Z, Lancelot E, Corot C, Canet-Soulas E, Letourneur D. A new macromolecular paramagnetic MR contrast agent binds to activated human platelets. Contrast Media Mol Imaging. Jul. 2007;2(4):178-88. PubMed PMID: 17828728. (NPL #35).
Saborowski O, Simon GH, Raatschen HJ, Wendland MF, Fu Y, Henning T, Baehner R, Corot C, Chen MH, Daldrup-Link HE. MR imaging of antigen-induced arthritis with a new, folate receptor-targeted contrast agent. Contrast Media Mol Imaging. Mar.-Apr. 2007;2(2):72-81. PubMed PMID: 17385788. (NPL #36).
Peukert D, Kaufels N, Laule M, Schnorr J, Carme S, Farr T, Schonenberger E, Taupitz M, Hamm B, Dewey M. Improved evaluation of myocardial perfusion and viability with the magnetic resonance blood pool contrast agent p792 in a nonreperfused porcine infarction model. Invest Radiol. Apr. 2007;42(4):248-55. PubMed PMID: 17351432. (NPL #37).
Su W, Mishra R, Pfeuffer J, Wiesmtiller KH, Ugurbil K, Engelmann J. Synthesis and cellular uptake of a MR contrast agent coupled to an antisense peptide nucleic acid—cell-penetrating peptide conjugate. Contrast Media. Mol Imaging. Jan.-Feb. 2007;2(1):42-9. PubMed PMID: 17318918. (NPL #38).
Wiart M, Carme S, Mal: W, Larsson HB, Neyran B, Canet-Soulas E. In vivo quantification of regional myocardial blood flow: validity of the fast-exchange approximation for intravascular T1 contrast agent and long inversion time. Magn Reson Med. Aug. 2006;56(2):340-7. PubMed PMID: 16826607. (NPL #39).
Preda A, Novikov V, Möglich M, Floyd E, Turetschek K, Shames DM, Roberts TP, Corot C, Carter WO, Brasch RC. Magnetic resonance characterization of tumor microvessels in experimental breast tumors using a slow clearance blood pool contrast agent (carboxymethyldextran-A2-Gd-DOTA) with histopathological correlation. Eur Radiol. Nov. 2005;15(11):2268-75. Epub Jul. 13, 2005. PubMed PMID: 16012822. (NPL #40).
Dewey M, Kaufels N, Laule M, Schnorr J, Raynaud JS, Hamm B, Taupitz M. Magnetic resonance imaging of myocardial perfusion and viability using a blood pool contrast agent. Invest Radiol. Aug. 2004;39(8):498-505. PubMed PMID: 15257211. (NPL #41).
Nicolle GM, Tóth E, Schmitt-Willich H, Radtichel B, Merbach AE. The impact of rigidity and water exchange on the relaxivity of a dendritic MRI contrast agent. Chemistry. Mar. 1, 2002;8(5):1040-8. PubMed PMID: 11891890. (NPL #42).
Fonchy E, Lahrech H, François-Joubert A, Dupeyre R, Benderbous S, Corot C, Farion R, Rubin C, Décorps M, Rémy C. A new gadolinium-based contrast agent for magnetic resonance imaging of brain

(56) References Cited

OTHER PUBLICATIONS tumors: kinetic study on a C6 rat glioma model. J Magn Reson Imaging. Aug. 2001;14(2):97-105. PubMed PMID: 11477666. (NPL #43).

Dedieu V, Fau P, Otal P, Renou JP, Emerit V, Joffre F, Vincensini D. Rapid relaxation times measurements by MRI: an in vivo application to contrast agent modeling for muscle fiber types characterization. Magn Reson Imaging. Dec. 2000:18(10):1221-33. PubMed PMID: 11167042. (NPL #44).

Parodi JC, Ferreira LM. Gadolinium-based contrast: an alternative contrast agent for endovascular interventions. Ann Vasc Surg. Sep. 2000;14(5):480-3. PubMed PMID: 10990558. (NPL #45).

Baumann D, Rudin M. Quantitative assessment of rat kidney function by measuring the clearance of the contrast agent Gd(DOTA) using dynamic MRI. Magn Reson Imaging. Jun. 2000;18(5):587-95. PubMed PMID: 10913720. (NPL #46).

Canet EP, Casali C, Desenfant A, An MY, Corot C, Obadia JF, Revel D, Janier MF. Kinetic characterization of CMD-A2-Gd-DOTA as an intravascular contrast agent for myocardial perfusion measurement with MRI. Magn Reson Med. Mar. 2000;43(3):403-9. PubMed PMID: 10725883. (NPL #47).

Kroft LJ, Doornbos J, van der Geest RJ, de Roos A. Blood pool contrast agent CMD-A2-Gd-DOTA-enhanced MR imaging of infarcted myocardium in pigs. J Magn Reson Imaging. Aug. 1999;10(2):170-7. PubMed PMID: 10441021. (NPL #48).

Kroft LJ, Doornbos J, Benderbous S, de Roos A. Equilibrium phase MR angiography of the aortic arch and abdominal vasculature with the blood pool contrast agent CMD-A2-Gd-DOTA in pigs. J Magn Reson Imaging. Jun. 1999;9(6):777-85. PubMed PMID: 10373025. (NPL #49).

Casali C, Janier M, Canet E, Obadia JF, Benderbous S, Corot C, Revel D. Evaluation of Gd-DOTA-labeled dextran polymer as an intravascular MR contrast agent for myocardial perfusion. Acad Radiol. Apr. 1998;5 Suppl 1:S214-8. PubMed PMID: 9561084. (NPL #50).

Loubeyre P, Canet E, Zhao S, Benderbous S, Amiel M, Revel D. Carboxymethyl-dextran-gadolinium-DTPA as a blood-pool contrast agent for magnetic resonance angiography. Experimental study in rabbits. Invest Radiol. May 1996;31(5):288-93. PubMed PMID: 8724128. (NPL #51).

Schwizer W, Fraser R, Maecke H, Siebold K, Funck R, Fried M. Gd-DOTA as a gastrointestinal contrast agent for gastric emptying measurements with MRI. Magn Reson Med. Apr. 1994;31(4):388-93. PubMed PMID: 8208114. (NPL #52).

Marchal G, Ni Y, Van Damme B, Van Hecke P, Michiels J, Yu J, Zhang X, Baert AL. Role of contrast agent perfusion and of diffusion in the NMR signal enhancement of liver lesions. J Comput Assist Tomogr. Sep.-Oct. 1992;16(5):690-8. PubMed PMID: 1522258. (NPL #53).

Schaefer M, Meyer D, Beaute S, Doucet D. A new macrocyclic MRI contrast agent: Gd MCTA complex. Magn Reson Med. Dec. 1991;22(2):238-41. PubMed PMID: 1812352. (NPL #54).

Elizondo G, Fretz CJ, Stark DD, Rocklage SM, Quay SC, Worah D, Tsang YM, Chen MC, Ferrucci JT. Preclinical evaluation of MnDPDP: new paramagnetic hepatobiliary contrast agent for MR imaging. Radiology. Jan. 1991;178(1):73-8. PubMed PMID: 1898538, (NPL #55).

Runge VM, Kaufman DM, Wood ML, Adelman LS, Jacobson S. Experimental trials with Gd(DO3A)—a nonionic magnetic resonance contrast agent. Int J Rad Appl Instrum B. 1989;16(6):561-7. PubMed PMID: 2606711. (NPL #56).

Meyer D, Schaefer M, Bonnemain B. Gd-DOTA, a potential MRI contrast agent. Current status of physicochemical knowledge. Invest Radiol. Sep. 1988;23 Suppl 1:S232-5. PubMed PMID: 3198351. (NPL #57).

Lorenzo-Lamosa et al., Design of microencapsulated chitosan microspheres for colonic drug delivery. J Control Rel, 52: 109-118, 1998. (NPL #58).

Dressman, J. B., Amidon, C., Reppas, C. and Shah, V. P., Dissolution testing as a prognostic tool for oral drug absorption: Immediate release dosage forms, Pharm Res, 15: 11-22, 1998. (NPL #59).

Gliko-Kabir, I., Yagen, B., Penhasi, A. and Rubinstein, A., Phosphated crosslinked guar for colon-specific drug delivery. I. Preparation and physicochemical characterization. J Control Rel, 63: 121-127, 2000. (NPL #60).

Rama Prasad, Y. V., Krishnaiah, Y. S. R. and Satyanarayana, S., In vitro evaluation of guar gum as a carrier for colon-specific drug delivery. J Control Rel, 51: 281-287, 1998. (NPL #61).

Milojevic, S., Newton, J. M., Cummings, J. H., Gibson, G. R., Botham, R. L., Ring, S. C., Stockham, M. and Allwood, M. C., Amylose as a coating for drug delivery the colon: Preparation and in vitro evaluation using 5-aminosalicylic acid pellets. J Control Rel, 38: 75-84, 1996. (NPL #62).

Tozaki, H., Odoriba, T., Okada, N., Fujita, T., Terabe, A., Suzuki, T., Okabe, S., Murnishi, S, and Yamamoto, A., Chitosan capsules for colon-specific drug delivery: enhanced localization of 5-aminosalicylic acid in the large intestine accelerates healing of TNBS-induced colitis in rats. J Control Rel, 82, 51-61, 2002. (NPL #63).

Atyabi et al, In vitro evaluation and modification of pectinate gel beads containing trimethyl chitosan, as a multi-particulate system for delivery of water-soluble macromolecules to colon. Carbohyd. Polymers, 2005, 61, 39-51. (NPL #64).

Liu et al, Pectin-based systems for colon-specific drug delivery via oral route. Biomaterials 2003, 24, 3333-3343. (NPL #65).

Wakerly et al., Pectin/Ethylcellulose Film Coating Formulations for Colonic Drug Delivery. Pharm. Res., 1996, 13 (8), 1210-1212. (NPL #66).

Wei et al., PDA Journal of Pharmaceutical Science and Technology, vol. 61, No. 2, Mar.-Apr. 2007, 121-130. (NPL #67).

Bragger et al., Investigations into the azo reducing activity of a common colonic microorganism. Int J Pharm, 157: 61-71, 1997. (NPL #68).

\* cited by examiner

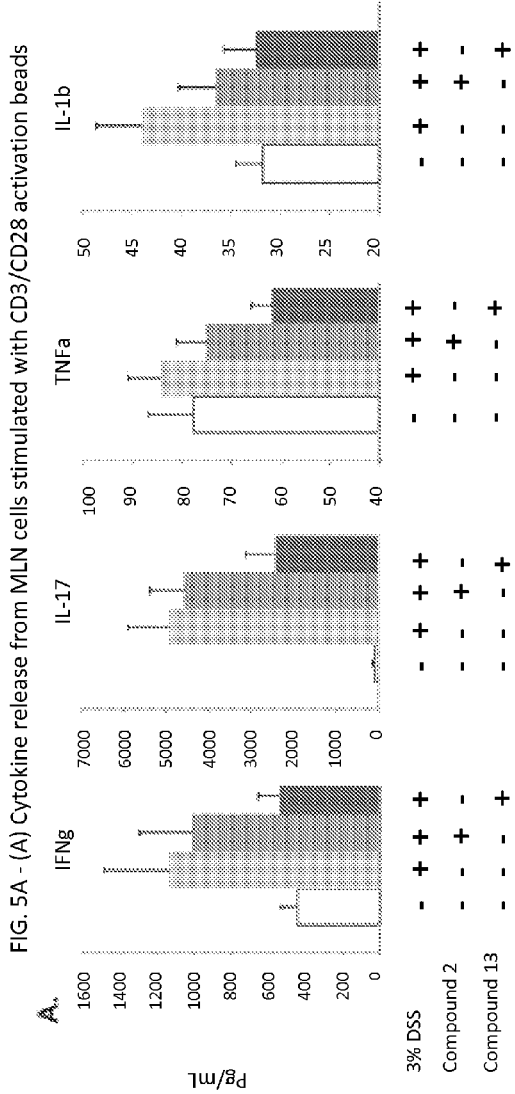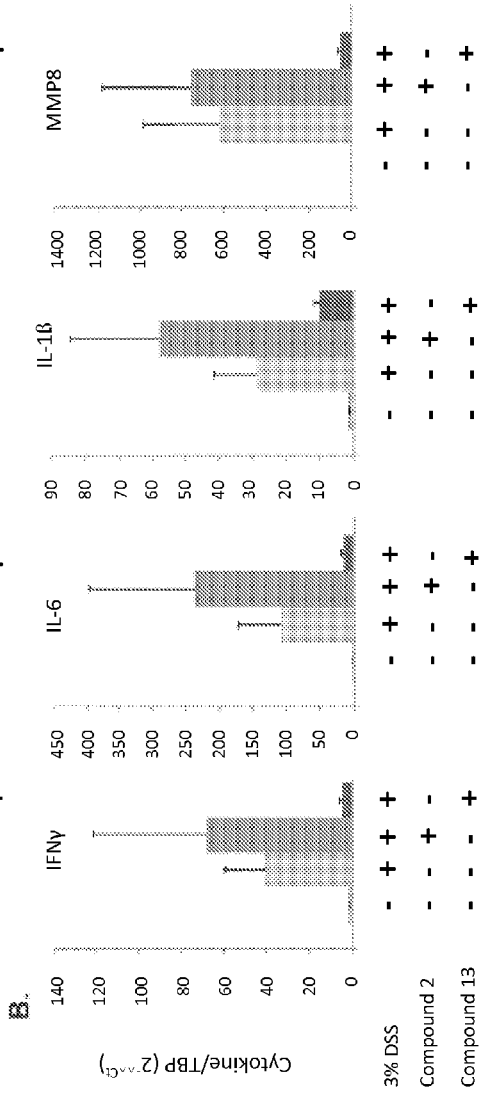
FIG. 5A - (A) Cytokine release from MLN cells stimulated with CD3/CD28 activation beads
FIG. 5B - (B) qRT-PCR analysis of colonic cytokine mRNA expression.

METHOD AND COMPOSITIONS FOR TARGETED DRUG DELIVERY TO THE LOWER GI TRACT

CROSS REFERENCE TO RELATED APPLICATION

This application claims priority from U.S. Provisional Application Ser. No. 61/821,166, filed May 8, 2013, the contents of which are incorporated herein by reference.

STATEMENT OF GOVERNMENT INTEREST

This invention was made with government support under Grant Nos. P30 CA023074; R01 CA097360; R01 CA123547; R01 DK041274; R01 DK067286 and R37 DK033209 awarded by the National Institutes of Health (NIH). The government has certain rights in the invention

FIELD OF THE INVENTION

This invention relates generally to the field of medicine, and more specifically to methods and compositions for targeted delivery of substances to the lower GI tract. The invention has particular utility for delivery of drugs for treating or preventing diseases of the colon, and in particular, inflammatory bowel disease, microscopic colitis, eosinophilic colitis and will be described in connection with such utility, although other utilities are contemplated.

BACKGROUND OF THE DISCLOSURE

Millions of people in the world suffer from inflammatory bowel disease (IBD). IBD is a collective term used to describe two gastrointestinal disorders of unknown etiology; Crohn's disease (CD) and ulcerative colitis (UC). Both diseases appear to result from the unrestrained activation of an inflammatory response in the intestine. Ulcerative colitis occurs in the large intestine, while Crohn's disease can involve any segment of the gastrointestinal tract. It has been suggested that the pathogenesis of IBD is multifactorial involving susceptibility genes and environmental factors. Although the causative triggers remain unclear, the role of a persistent and likely dysregulated mucosal immune response is central to the pathogenesis of IBD. It remains unclear whether the persistent inflammation, an intrinsic feature of IBD, reflects a primary aberration in mucosal response or results from an inappropriate persistent stimulation.

The course and prognosis of IBD varies widely. For most patients, it is a chronic condition with symptoms lasting for months to years. IBD is most commonly diagnosed in young adults, but can occur at any age. The clinical symptoms of IBD include intermittent rectal bleeding, fever, abdominal pain, and diarrhea, which may range from mild to severe. Additional common signs of IBD are anemia and weight loss. 10 to 15% of all IBD patients will require surgery over a ten year period. Protracted IBD is a risk factor for colon cancer, and the risk begins to rise significantly after eight to ten years of IBD.

Bowel disorders such as IBD are a significant medical problem, and improved methods of treatment are necessary as no completely satisfactory treatments are currently available.

The first line therapy that often is used for treatment of IBD is 5-aminosalicylic acid (5-ASA). A key to successful treatment is to deliver a high concentration of 5-ASA to the site of inflammation. However, when 5-ASA is administered orally without a carrier or protector, it is nearly completely systemically absorbed in the proximal small intestine prior to reaching the affected area, and is extensively metabolized in intestinal epithelial cells and the liver; it is then excreted in the urine, which may predispose patients to the development of a nephrotic syndrome as a side effect. Therefore, strategies to "protect" orally administered 5-ASA from absorption until it reaches the colon have been developed. These strategies include the use of prodrug, delayed-release formulations (coat the drug with polymers), controlled-release formulations (formulate the 5-ASA as ethylcellulose-coated microgranules), and, more recently, sophisticated formulations that combine both delayed-release and sustained-release mechanisms.

Various strategies have been proposed for targeting orally administered drugs to the colon, including: covalent linkage of a drug with a carrier, including those that enhance stability as well as increasing hydrophilicity; coating with pH-sensitive polymers; formulation of timed released systems; exploitation of carriers that are degraded specifically by colonic bacteria; bioadhesive systems; and osmotic controlled drug delivery systems. Various prodrugs (sulfasalazine, ipsalazine, balsalazide, and olsalazine) have been developed that are aimed to deliver 5-aminosalicylic acid (5-ASA) for localized chemotherapy of inflammatory bowel disease (IBD). Microbially degradable polymers, especially azo-crosslinked polymers, have been investigated for use as coatings for drugs targeted to the colon. Certain plant polysaccharides such as amylose, inulin, pectin, and guar gum remain unaffected in the presence of gastrointestinal enzymes and have been explored as coatings for drugs for the formulation of colon-targeted drug delivery systems. Additionally, combinations of plant polysaccharides with crustacean extract, including chitosan or derivatives thereof, are proving of interest for the development of colonic delivery systems.

The concept of using pH as a trigger to release a drug in the colon is based on the pH conditions that vary continuously down the gastrointestinal tract (GIT). Time-dependent drug delivery systems have been developed that are based on a principle of preventative release of drug until 3-hours after leaving the stomach. Redox sensitive polymers and bioadhesive systems have also been exploited to deliver the drugs into the colon. Other systems for drug delivery to the colon, pH-dependent systems, exploit the generally accepted view that pH of the human GIT increases progressively from the stomach (pH 1-which increases to during digestion), small intestine (pH 6-7) at the site of digestion and it increases to 7-8 in the distal ileum. The coating of pH-sensitive polymers to the tablets, capsules or pellets provides delayed release and protects the active drug from gastric fluid. The polymers used for colon targeting, however, should be able to withstand the lower pH values of the stomach and of the proximal part of the small intestine and also be able to disintegrate at the neutral or slightly alkaline pH of the terminal ileum and preferably at the ileocecal junction.

Lorenzo-Lamosa et al. (Design of microencapsulated chitosan microspheres for colonic drug delivery. J Control Rel, 52: 109-118, 1998) prepared and demonstrated the efficacy of a system, which combines specific biodegradability and pH dependent release behaviour. The system consists of chitosan microcores entrapped within acrylic microspheres containing diclofenac sodium as a model drug. The drug was effectively entrapped within the chitosan microcores using spray drying and then microencapsulated into Eudragit™ L-100 and Eudragit™ S-100 acrylic polymers using an oil-in-oil solvent evaporation method. Release of the drug from chitosan multireservoir system was adjusted by changing the chitosan molecular weight or the type of chitosan salt. Furthermore, by coating the chitosan microcores with Eudragit™, perfect pH-dependent release profiles were attained. Similarly, melt extrusion of a drug with various Eudragit™ polymers in the presence or absence of chitosan, gelling agents or the like has the potential to enable colon-specific release.

Other suitable polymers that are slightly permeable to the active ingredient and water, and exhibit a pH-dependent permeability, include, but are not limited to, EUDRAGIT™ RL, EUDRAGIT™ RS, EUDRAGIT™ L, EUDRAGIT™ S, and EUDRAGIT™ E. See also Dressman, J. B., Amidon, C., Reppas, C. and Shah, V. P., Dissolution testing as a prognostic tool for oral drug absorption: Immediate release dosage forms, Pharm Res, 15: 11-22, 1998.

Polysaccharides, which retain their integrity because they are resistant to the digestive action of gastrointestinal enzymes also have been proposed for encapsulating drugs for colonic drug delivery. The matrices of polysaccharides are assumed to remain intact in the physiological environment of stomach and small intestine but once they reach in the colon, they are acted upon by the bacterial polysaccharidases and this action results in the degradation of the matrices. This family of natural polymers has an appeal to the area of drug delivery as it is comprised of polymers with a large number of derivatizable groups, a wide range of molecular weights, varying chemical compositions, and for the most part, a low toxicity and biodegradability, yet a high stability. The most favourable property of these materials is that they are already approved as pharmaceutical excipients. A large number of polysaccharides such as amylose, guar gum, pectin, chitosan, inulin, cyciodextrins, chondroitin sulphate, dextrans and locust bean gum, as well as modifications thereof, have been investigated for their use in colon-targeted drug delivery systems. The most important fact in the development of polysaccharide derivatives for colon targeted drug delivery is the selection of a suitable biodegradable polysaccharide. As these polysaccharides are usually soluble in water, they must be made water insoluble by crosslinking or hydrophobic derivatisation.

Guar gum is hydrophilic in nature and swells in cold water, forming viscous colloidal dispersions, or sols. This gelling property retards release of the drug from the dosage form and renders it susceptible to degradation in the colonic environment. Homogenized and diluted feces from a human source were incubated with the guar gum to investigate the degradation of the polysaccharide sol by intestinal microflora. It produced a rapid decrease in viscosity and an increase in pH (i.e. became more basic) while no such results were observed when it was incubated with autoclaved fecal homogenates. Guar gum was crosslinked with increasing amounts of trisodium trimetaphosphate to reduce its swelling properties for use as a vehicle in oral delivery formulations. As a result of the crosslinking procedure guar gum lost its non-ionic nature and became negatively charged. This was demonstrated by methylene blue adsorption studies and swelling studies in sodium chloride solutions with increasing concentrations in which the hydrogels' network collapsed (Gliko-Kabir, I., Yagen, B., Penhasi, A. and Rubinstein, A., Phosphated crosslinked guar for colon-specific drug delivery. I. Preparation and physico-chemical characterization. J Control Rel, 63: 121-127, 2000). Crosslinked guar gum products were analysed to check the efficacy as a colon-specific drug carrier and it was found that the product which was crosslinked with 0.1 molar equivalent of trisodium trimetaphosphate was able to prevent the release of 80% of its hydrocortisone load for at least hours in PBS (pH 6.4). When a mixture of α-galactosidase and β-mannanase was added to the buffer solution, an enhanced release was observed. In vivo degradation studies in the rat caecum showed that despite the chemical modification of guar gum, it retained its enzyme-degrading properties in a crosslinker concentration dependent manner. A novel tablet formulation for oral administration using guar gum as the carrier and indomethacin as a model drug has been investigated for colon targeted drug delivery using in vitro methods. Drug release studies under conditions simulating the gastrointestinal transit have shown that guar gum protects the drug from being released completely in the physiological environment of stomach and small intestine. Studies in pH 6.8 PBS containing rat caecal contents have demonstrated the susceptibility of guar gum to the colonic bacterial enzyme action with consequent drug release (Rama Prasad, Y. V., Krishnaiah, Y. S. R. and Satyanarayana, S., In vitro evaluation of guar gum as a carrier for colon-specific drug delivery. J Control Rel, 51: 281-287, 1998). Colon-specific drug delivery also has been proposed using dried amylose films to encapsulate pharmaceutical formulations. Amylose, one of the major fractions of starch, possesses the ability to form films through gelation, when prepared under appropriate conditions. The microstructure of the film is potentially resistant to the action of pancreatic α-amylase but is digested by amylases of the colonic microflora. However, under simulated gastrointestinal conditions, coatings made solely of amylose will become porous and allow drug release. Incorporation of insoluble polymers into the amylose film, to control amylose swelling, provides a solution to this problem. A range of cellulose and acrylate based copolymers were assessed, of which a commercially available ethylcellulose (Ethocel) was found to control the swelling most effectively. The in vitro dissolution of various coated pellets under simulated gastric and small intestinal conditions, using commercially available pepsin and pancreatin was determined and demonstrated the resistance of the amylose-Ethocel coat (1:4) to such conditions over a period of 12 h (Milojevic, S., Newton, J. M., Cummings, J. H., Gibson, G. R., Botham, R. L., Ring, S. C., Stoekham, M. and Allwood, M. C., Amylose as a coating for drug delivery the colon: Preparation and in vitro evaluation using 5-aminosalicylic acid pellets. J Control Rel, 38: 75-84, 1996).

Chitosan is a high molecular weight polycationic polysaccharide derived from naturally occurring chitin by alkaline deacetylation. Chitosan has favourable biological properties such as nontoxicity, biocompatibility, and biodegradability. Similar to other polysaccharides, it also undergoes degradation by the action of colonic microflora, and hence poses its candidature for colon targeted drug delivery. Tozaki et al. (Tozaki, H., Odoriba, T., Okada, N., Fujita, T., Terabe, A., Suzuki, T., Okabe, S., Mumishi, S, and Yamamoto, A., Chitosan capsules for colon-specific drug delivery: enhanced localization of 5-aminosalicylic acid in the large intestine accelerates healing of TNBS-induced colitis in rats. J Control Rel, 82, 51-61, 2002) developed colon-specific insulin delivery with chitosan capsules. In vitro drug release experiments from chitosan capsules containing 5(6)-carboxyfluorescein (CF) were carried out by a rotating basket method with slight modifications. The intestinal absorption of insulin was evaluated by measuring the plasma insulin levels and its hypoglycaemic effects after oral administration of the chitosan capsules containing insulin and additives. Little release of CF from the capsules was observed in an artificial gastric juice (pH 1), or in an artificial intestinal juice (pH 7). However, the release of CF was markedly increased in the presence of rat caecal contents. This group further evaluated colon-specific insulin delivery using chitosan capsules. It was found that these were stable in the stomach and small intestine but degraded by micro-organisms in rat caecal contents upon entering into the colon, proving their utility as carriers for colon targeted drug delivery of peptide and non-peptide drugs.

Pectin, a predominantly linear polymer of mainly α-(1→4)-linked D-polygalacturonic acid residues, has been widely investigated as a colon-specific drug delivery entity. It can be broken down by pectinase enzymes produced by anaerobic bacteria of the colon and can control drug release by this principle (Atyabi et al, Carbohyd. Polymers, 2005, 61, 39-51). As pectin is water soluble, efficient colonic delivery requires that the solubility is controlled. Liu et al. (Liu et al, Biomaterials 2003, 24, 3333-3343) demonstrated promising drug delivery potential when pectin was combined with water-insoluble polymers. Previously, Wakerly et al. (Wakerly et al., Pharm. Res., 1996, 13 (8), 1210-1212) identified that a combination of ethylcellulose and pectin could provide protection of a drug in the upper GI tract while allowing enzymatic breakdown and drug release in the colon. Wei et al. (Wei et al., PDA Journal of Pharmaceutical Science and Technology, Vol 61, No. 2, March-April 2007, 121-130) demonstrated that colon-specific controlled release of the water-soluble anticancer agent, 5-fluorouracil, was possible when incorporated into pellets that were coated with various proportions of pectin and ethycellulose (Surlease®).

Redox potential is an expression of the total metabolic and bacterial activity in the colon and it is believed to be insensitive to dietary changes. The mean redox potential in proximal small bowel is −67±90 mV, in the distal small bowel is −196±97 mV and in the colon is −145±72 mV. Thus, microflora-induced changes in the redox potential can be used as a highly selective mechanism for targeting to the colon. Bragger et al. (Investigations into the azo reducing activity of a common colonic microorganism. Int J Pharm, 157: 61-71, 1997) carried out investigations into the azo reducing activity, which could enlighten some factors affecting the bacterial reduction (cleavage) of azo compounds. A common colonic bacterium, *Bacteroides fragilis*, was used as test organism, and the reductions of azo dyes amaranth, Orange II, tartrazine, and a model azo compound, 4,4'-dihydroxyazobenzene, were studied. It was found that the azo compounds were reduced at different rates, and the rate of reduction could be correlated with the redox potential of the azo compounds. Disulfide compounds can also undergo degradation due to the influence of redox potential in the colon. Noncrosslinked redox-sensitive polymers containing an azo and/or a disulfide linkage in the backbone have been synthesised (Schacht, E. and Wilding, I. R., Process for the preparation of azo- and/or disulfide-containing polymers. Patent: WO 9111175).

The foregoing discussion of prior art derives primarily from U.S. patent publication 2010/0255087 to Coulter who proposed oral pharmaceutical compositions comprising mini-capsules containing one or more active pharmaceutical compounds in a liquid, semi-solid or solid core mini-capsule format, wherein the mini-capsules have release profiles intended to release the active pharmaceutical compound at one or more sites along the gastro-intestinal tract where absorption is maximized or therapeutic efficacy is maximized. More particularly, according to the '087 publication, the mini-capsules are formed of or have coatings formed of materials that are sensitive to one or more pH, time, thickness, erosion and bacterial breakdown to achieve a desired release of active pharmaceutical agents along the gastro-intestinal tract.

SUMMARY OF THE DISCLOSURE

The present disclosure provides improvements in oral pharmaceutical compositions by providing compounds comprising a base or scaffold carrier to which a drug or prodrug is fixed or covalently attached. The compound, which includes azo or disulfide bonds when taken orally in pill or capsule or suspension or liquid form, travels through the GI tract of a patient to the lower GI tract where bacterial azoreductase enzymes cleave azo or disulfide bonds, releasing the drug or prodrug from the base or scaffold carrier, permitting delivery of the drug to the vicinity of the target cell type in the GI tract. The base or scaffold, which remains as a by-product, passes out of the GI tract in the feces, causing no side effects. As a result, a high concentration of drug is delivered to a target site, permitting a lower dose, while enhancing the therapeutic effect of the drug with fewer side effects.

BRIEF DESCRIPTION OF THE DRAWINGS

Further features and advantages of the present disclosure will be seen from the following detailed description, taken in conjunction with the accompanying drawings, wherein:

FIG. 5A shows cytokine release and FIG. 5B shows cytokine mRNA expression in accordance with the present disclosure.

DETAILED DESCRIPTION

The pharmaceutical composition, in accord with the present disclosure, comprises a base or carrier scaffold formed of a food grade polyhydroxol compound, preferably a sugar, more preferably an octaalkyne, having a linker as will be described below, to which a drug or prodrug is fixed or covalently bonded.

Various food grade polyhydroxol compounds are available commercially and advantageously may be used according to the present disclosure, including, but not limited to:

monosaccharides, such as triose, tetrose, pentose, hexose, and heptose aldols, ketoses, sugar alcohols, or sugar acids;
disaccharides, for one example, sucrose;
trisaccharides, for one example, raffinose;
tetrasaccharides, for one example, stachyose;
sugar polymers; and
cyclitols, for one example, myo-inositol.

The linker, one or more copies of which are covalently bonded to the polyhydroxol compound, may be comprised of a straight chain, a branched, and/or a cyclic segment composed of a hydrocarbon, a heteroatom-interrupted hydrocarbon, for one example, a polyethyleneglycol, an arene, or a heterocyclic ring, for one example, a triazole.

The drug or prodrug will comprise a pharmaceutical compound, for example, para-aminophenol, 5-aminosalicylic acid, 5-fluorouracil, and imiquimod, as such or in a prodrug form due to chemical attachment to the scaffold through the linker. A preferred pharmaceutical compound intended for delivery of 5-aminosalicylic acid (5-ASA) to the lower gastrointestinal tract comprises eight (8) molecules of 5-ASA in the form of a prodrug linked to a sucrose-derived octaalkyne, as compound I shown in FIG. 1.

Figure 2:
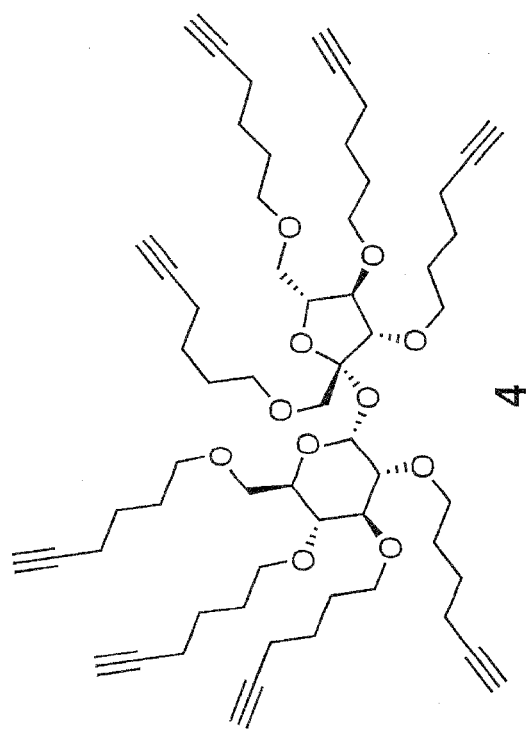
FIG. 2 illustrates a first step and FIG. 3 a second step of a reaction scheme for synthesizing one specific example of a pharmaceutical compound in accordance with one embodiment of the disclosure.
Figure 2:
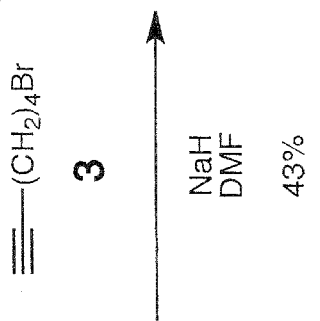
Figure 2:
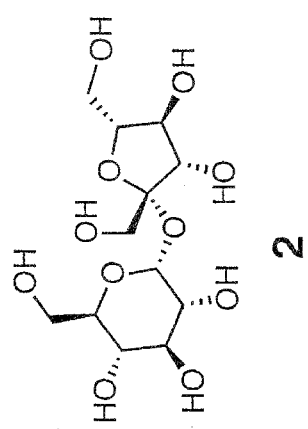

Compound I is synthesized as follows:

First, sucrose is reacted with sodium hydride and 10-bromo-1-decyne to produce an octaalkyne (FIG. 2).

Figure 1:
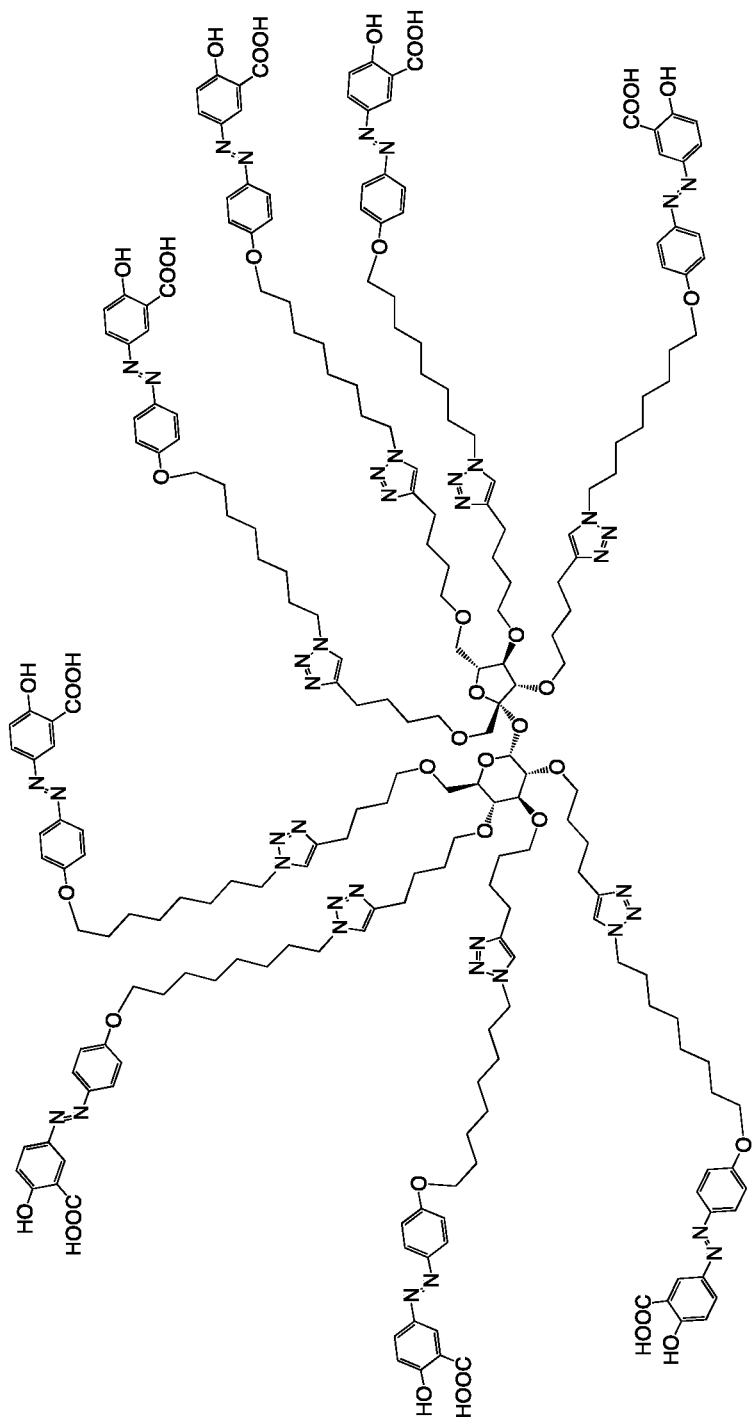
FIG. 1 shows a preferred compound in accordance with one embodiment of the disclosure.
Figure 3:
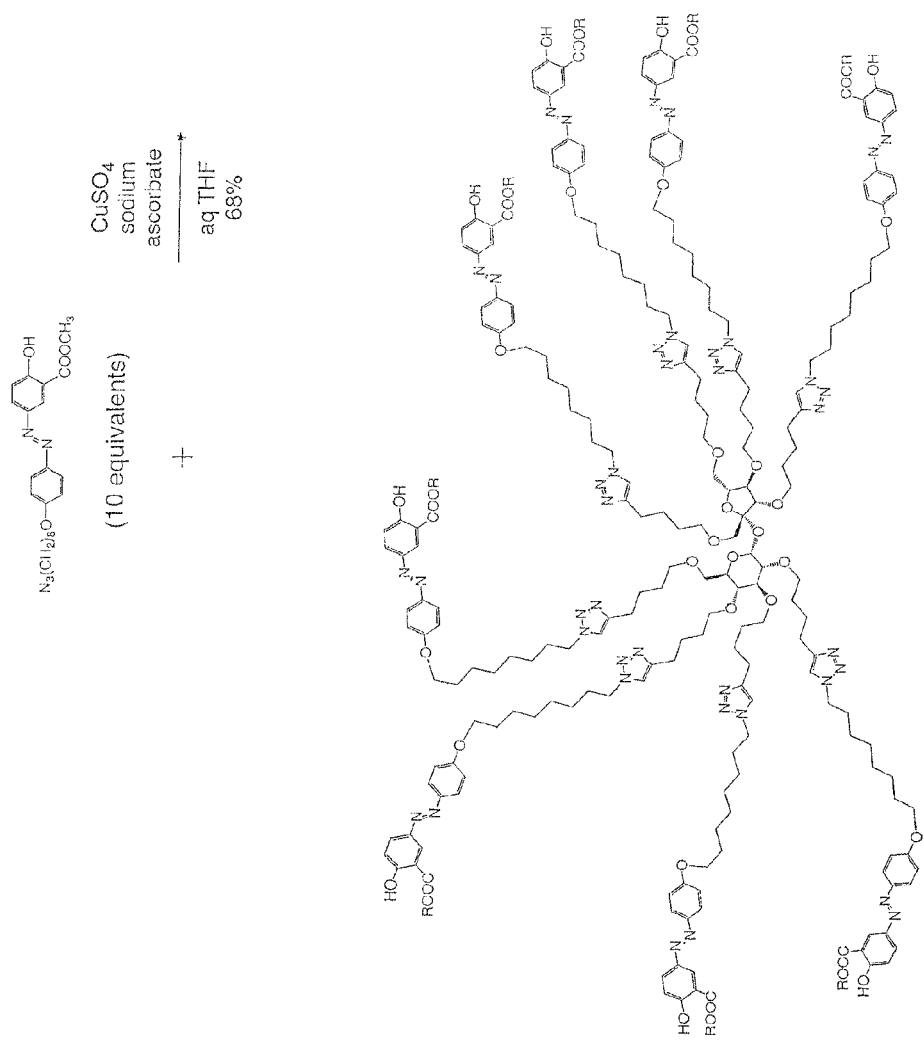
Figure 4:
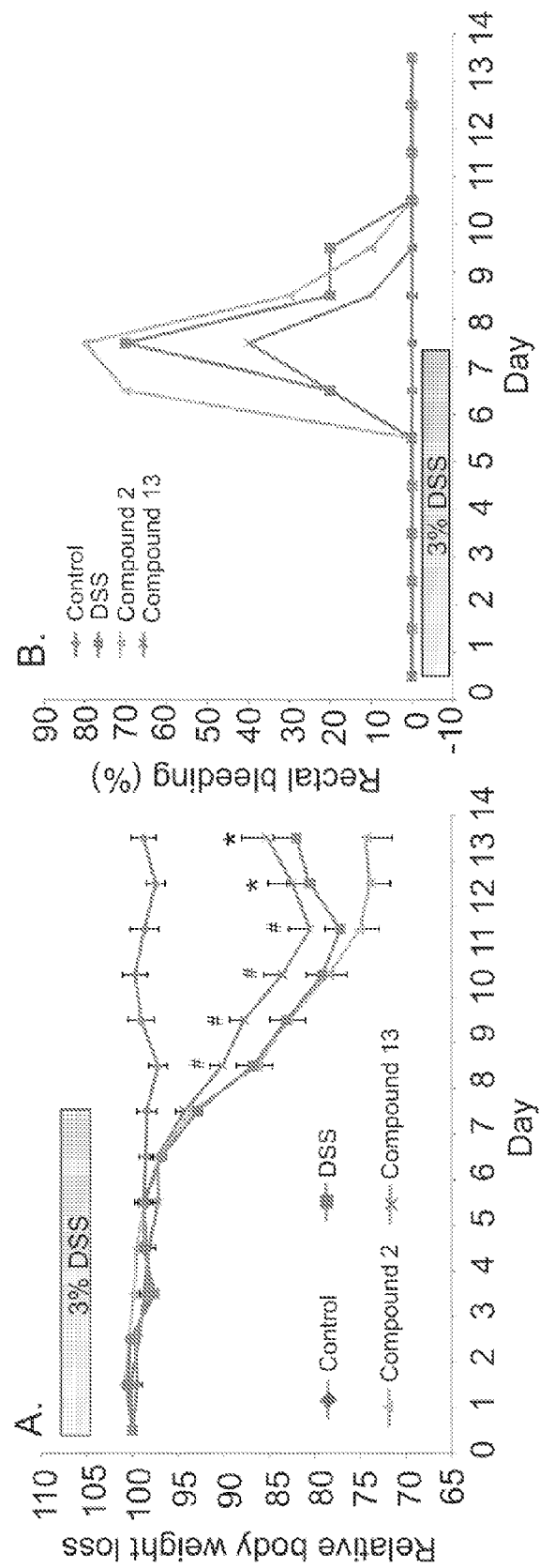
FIG. 4A plots relative body weight loss and FIG. 4B plots rectal bleeding following delivery of 5-aminosalicylic acid (5 ASA) over time.

Then, an excess of the azide depicted in FIG. 2 is reacted with the octaalkyne from FIG. 1 in the presence of copper sulfate and sodium ascorbate in tetrahydrofuran to produce compound I. (FIG. 3).

The resulting compound I may be delivered to the patient orally in pill or suspension form, where it travels through the GI tract to the lower GI, where bacterial azoreductase enzymes cleave the azo bonds, releasing the drug 5-aminosalicylic acid from its prodrug form. The remaining scaffold/linker byproduct passes out of the GI in the feces, having caused no side effects. This same mode of drug delivery may be utilized for related prodrug forms of para-aminophenol, 5-fluorouracil, and imiquimod, among other possibilities. Attachment to the scaffold, along with the prodrug, of one or more copies of a ligand targeted to a cell type of interest, permits delivery of a pharmaceutical compound to the vicinity of the cell type of interest in the GI tract. This delivery system enhances the therapeutic effect by placing the highest concentration of drug where it is most useful. This is demonstrated by studies performed as reported below.

EXAMPLES

The following examples illustrate preparation and use of a carrier scaffold/drug or prodrug in accordance with the present disclosure.

Example I

A) Preparation of the Octaalkyne

Octa-O-(5-hexyn-1-yl)-β-D-fructofuranosyl-α-D-glucopyranoside

To a suspension of NaH (330 mg, 13.7 mmol) in dry dimethylformamide (DMF, 10 mL) under argon were added sucrose (200 mg, 0.58 mmol), 6-bromo-1-hexyne[33] (1.13 g, 6.97 mmol), and tetrabutylammonium bromide (50 mg, 0.15 mmol). The mixture was stirred at room temperature for 48 h. The reaction was quenched with sat $NH_4Cl$ and the mixture extracted with ethyl acetate (3×15 mL). The combined organic extracts were washed with water, brine, dried over $Na_2SO_4$, and filtered. Removal of volatiles in vacuo afforded a residue that was subjected to silica gel chromatography (63-210 μm) using ethyl acetate/hexanes (2:8) as elutant. This afforded 250 mg (0.25 mmol, 43%) of product as a colorless oil, $R_f$ 0.6 (ethyl acetate/hexanes, 3:7), $[\alpha]_D^{25}$ 17.0 (c 0.5, $CHCl_3$); IR (cm$^{-1}$) 3308, 2928, 2854, 1213, 1152, 1094; $^1$H NMR (500 MHz, $CDCl_3$) δ 1.57-1.71 (m, 32H), 1.95 (m, 8H), 2.18-2.23 (m, 16H), 3.17 (dd, J=9.5 Hz, J=3.4 Hz, 1H), 3.28 (t, J=9.5 Hz, 1H), 3.35-3.71 (m, 20H), 3.77-3.92 (m, 5H), 4.07 (d, J=7.2 Hz, 1H), 5.50 (d, J=3.8 Hz, 1H); $^{13}$C NMR (125 MHz, $CDCl_3$) δ 18.3, 24.7, 25.3, 28.6, 28.7, 29.1, 29.2, 29.6, 31.7, 62.3, 68.4, 68.5, 69.5, 70.2, 70.5, 70.6, 70.8, 71.0, 71.1, 71.7, 72.3, 72.4, 72.7, 79.5, 80.5, 81.6, 82.9, 84.0, 84.2, 84.3, 89.9, 104.3; HRMS (MALDI-TOF) calculated for $C_{60}H_{86}NaO_{11}$ [M+Na]$^+$ 1005.6068, observed 1005.6068.

B) Preparation of Compound I 1-(8-Bromooctyloxy)-4-nitrobenzene

Anhydrous $K_2CO_3$ (5.50 g, 39.8 mmol) was added to a stirred solution of 4-nitrophenol (3.69 g, 26.5 mmol) and 1,8-dibromooctane (36.00 g, 132.1 mmol) in acetone. The reaction mixture was heated at reflux 12 h, then cooled to ambient temperature and filtered. The residue was washed with acetone (3×15 mL) and the combined organic layers evaporated in vacuo. The residue was dissolved in EtOAc (50 mL), the solution washed with water (2×20 mL), brine, dried over $Na_2SO_4$, filtered, volatiles evaporated in vacuo, and the residue subjected to column chromatography on silica gel (230-400 mesh) using hexanes as elutant to afford 7.75 g (23.5 mmol, 89%) of product as a low melting solid, mp 39-40° C. $^1$H NMR (500 MHz, $CDCl_3$) δ 1.35-1.50 (m, 8H), 1.79-1.89 (m, 4H), 3.41 (t, J=6.5 Hz, 2H), 4.04 (t, J=6.5 Hz, 2H), 6.93 (d, J=10 Hz, 2H), 8.18 (d, J=9.5, 2H); $^{13}$C NMR (125 MHz, $CDCl_3$) δ 27.9, 28.5, 28.8, 29.0, 29.2, 32.6, 33.9, 68.7, 114.3, 125.8, 129.3, 141.2, 164.1; HRMS (EI) calculated for $C_{14}H_{20}BrNO_3$ [M]$^{+0}$ 329.6027, observed 329.6040.

4-(8-Bromooctyloxy)aniline

Into a glass hydrogenation vessel were added 1-(8-bromooctyloxy)-4-nitrobenzene (5.00 g, 15.1 mmol) and absolute ethanol (50 mL). Carefully, 10% Pd/C (0.5 g) was added, the vessel was charged with hydrogen (40 psi), and the mixture was shaken on a Pan hydrogenation apparatus. After 3 h the mixture was diluted with $CH_2Cl_2$ (25 mL), filtered through a Celite pad, and volatiles removed in vacuo to give 4.20 g (14.0 mmol, 93%), of as a pale pink solid, mp 61-63° C. This material was used without purification in the next reaction. $^1$H NMR (500 MHz, $CDCl_3$) δ 1.27-1.44 (m, 8H), 1.75-1.84 (m, 4H), 3.39 (t, J=5.0 Hz, 2H), 3.89 (t, J=6.5 Hz, 2H), 6.77-6.88 (m, 2H); $^{13}$C NMR (125 MHz, $CDCl_3$) δ 22.7, 25.9, 26.0, 28.1, 28.7, 29.2, 29.4, 31.8, 32.8, 34.0, 68.5, 115.7, 118.6, 135.2, 154.1; HRMS (ESI) calculated for $C_{14}H_{23}BrNO$ [M+H]$^+$ 300.0957, observed 300.0963.

5-((4-(8-Bromooctyloxy)phenyl)diazenyl)-2-hydroxybenzoic acid 4-(8-Bromooctyloxy)aniline (2.30 g, 7.7 mmol) was suspended in a mixture of concentrated hydrochloric acid (mL) and water (75 mL). The resulting solution was cooled to 0° C. in an ice bath. Sodium nitrite (0.83 g, 12.1 mmol) in water (10 mL) was added dropwise to the reaction mixture with rapid stirring over about 20 min. The reaction mixture was stirred for an additional 20 min while salicylic acid (3.68 g, 26.6 mmol) was dissolved in an aqueous NaOH solution (8.0 g NaOH in 100 mL $H_2O$). This basic salicylic acid solution was vigorously stirred at 0° C. and the solution of the diazonium salt added dropwise. The pH was maintained at 12-14 by adding 8M NaOH solution. After the addition was complete, the solution was allowed to warm to room temperature and was stirred for an additional 30 min. The mixture was diluted with EtOAc (100 mL), washed with water (3×20 mL), 5% $NaHCO_3$ (2×20 mL), brine, dried over $Na_2SO_4$, and filtered. Volatiles were removed in vacuo and the residue subjected to column chromatography on silica gel 60 (230-400 mesh) using EtOAc and methanol (98:2) as elutant. The product (1.40 g, 3.1 mmol, 40%) was obtained as a red-brown solid, mp 180-182° C. $^1$H NMR (500 MHz, $CDCl_3$) δ 1.25-1.44 (m, 8H), 1.72-1.85 (m, 4H), 3.38 (t, J=Hz, 2H), 3.93 (t, J=6.5 Hz, 2H), 6.86-6.91 (m, 3H), 7.69 (d, J=Hz, 2H), 7.84 (dd, J=10 Hz, Hz, 1H), 8.42 (s, 1H); $^{13}$C NMR (125 MHz, $CDCl_3$) δ 25.8, 25.9, 28.0, 28.5, 29.0, 29.1, 29.2, 31.7, 32.7, 33.9, 35.2, 68.1, 113.3, 118.4, 123.1, 124.0, 126.1, 127.5, 144.9, 146.5, 161.0; HRMS (ESI) calculated for $C_{21}H_{26}BrN_2O_4$ (M+H)$^+$ 449.1070, observed 449.1063.

5-((4-(8-Azidooctyloxy)phenyl)diazenyl)-2-hydroxybenzoic acid 5-((4-(8-Bromooctyloxy)phenyl)diazenyl)-2-hydroxybenzoic acid (2.50 g, 5.6 mmol) was dissolved in DMSO (40 mL) and NaN$_3$ (1.10 g, 16.9 mmol) was added slowly to the reaction mixture with stirring at room temperature. After 48 h, the mixture was diluted with EtOAc (100 mL), washed with water (4×20 mL), brine (20 mL), dried over Na$_2$SO$_4$, and filtered. Volatiles were removed in vacuo and the residue subjected to column chromatography on silica gel 60 (230-400 mesh) using EtOAc and methanol (98:2) as the elutant to give 2.10 g (5.1 mmol, 91%) of the product as a red-brown solid, mp 54-56° C. $^1$H NMR (500 MHz, CDCl$_3$) δ 1.27-1.58 (m, 8H), 1.62-1.64 (m, 2H), 1.81-1.86 (m, 2H), 3.31 (t, J=5 Hz, 2H), 4.06 (t, J=6.5 Hz, 2H), 6.88-7.01 (m, 3H), 7.84 (d, J=10 Hz, 2H), 7.91 (dd, J=15 Hz, 2.5 Hz, 1H), 8.47 (d, J=2.5 Hz, 1H); $^{13}$C NMR (125 MHz, CDCl$_3$+CD$_3$OD) δ 22.0, 25.3, 25.4, 28.5, 28.6, 28.8, 31.2, 50.8, 67.7, 114.1, 116.5, 117.5, 123.6, 126.2, 144.6, 146.2, 160.7, 175.0; HRMS (ESI) calculated for C$_{21}$H$_{26}$N$_5$O$_4$ (M+H)+412.1979, observed 412.1971.

Methyl 5-((4-(8-Azidooctyloxy)phenyl)diazenyl)-2-hydroxybenzoate

To a stirred solution of 5-((4-(8-azidooctyloxy)phenyl)diazenyl)-2-hydroxybenzoic acid (400 mg, 0.97 mmol) in acetone (20 mL) was added powdered anhydrous potassium carbonate (270 mg, 1.94 mmol). Dimethyl sulfate (92 mg, 0.97 mmol) was then added dropwise at room temperature. The reaction mixture was heated at reflux for 20 min and then allowed to cool to ambient temperature. Volatiles were removed in vacuo, the residue taken up in EtOAc (40 mL), the solution washed with water (2×20 mL), brine, dried over Na$_2$SO$_4$, and filtered. Volatiles were removed in vacuo and the residue subjected to column chromatography on silica gel 60 (230-400 mesh) using EtOAc and hexanes (95:5) as the elutant to give 210 mg (0.49 mmol, 50%) of the product as a yellow solid, mp 58-60° C. $^1$H NMR (500 MHz, CDCl$_3$) δ 1.39-1.51 (m, 8H), 1.64 (qt, 2H), 1.83 (qt, 2H), 3.28 (t, J=Hz, 2H), 4.02 (s, 3H), 4.05 (t, J=6.5 Hz, 2H), 7.88 (d, J=Hz, 2H), 8.07 (dd, J=Hz, 2.5 Hz, 1H), 8.42 (d, J=2.5 Hz, 1H), 11.06 (s, 1H); $^{13}$C NMR (125 MHz, CDCl$_3$) δ 25.9, 26.7, 28.8, 29.1, 29.2, 51.5, 52.5, 68.2, 112.4, 114.7, 118.3, 124.5, 126.0, 128.7, 145.5, 146.7, 161.5, 163.3, 170.3; HRMS (ESI) calculated for C$_{22}$H$_{28}$N$_5$O$_4$ (M+H)+426.2135, observed 426.2141.

2 Octatriazole-octaester

A mixture of THF and water (9:1, 20 mL) was degassed with argon for 10 min. Methyl 5-((4-(8-Azidooctyloxy)phenyl)diazenyl)-2-hydroxybenzoate (880 mg, 2.07 mmol) and octa-O-(5-hexyn-1-yl)-3-D-fructofuranosyl-α-D-glucopyranoside (200 mg, 0.203 mmol) were added and degassing was continued for 5 min. Copper sulfate (26 mg, 0.02 mmol, 10 mol %) and sodium ascorbate (64 mg, 0.04 mmol, 20 mol %) were added and the solution was stirred under argon. Progress of the reaction was monitored by TLC using 10% methanol in CH$_2$Cl$_2$ plus 0.1% ammonium hydroxide. After 12 h the mixture was diluted with EtOAc (50 mL), washed with water (3×50 mL), brine, dried over anhydrous Na$_2$SO$_4$, filtered, and volatiles removed in vacuo. The residue was subjected to column chromatography on silica gel 60 (230-400 mesh) eluted with 20% EtOAc and hexanes (250 mL) and with 10% methanol in CH$_2$Cl$_2$ plus 0.1% ammonium hydroxide to give 600 mg (0.137 mmol, 68%) of the product as a red-brown solid, mp 50-51° C. $^1$H NMR (500 MHz, CDCl$_3$) δ 1.20-1.75 (m, 144H), 2.56-2.84 (m, 16H), 3.10-4.10 (m, 13H), 3.75-4.15 (m, 40H), 4.25-4.30 (m, 16H), 5.49 (m, 1H), 6.90-7.10 (m, 24H), 7.30-7.40 (m, 8H), 7.90-8.10 (m, 24H), 8.35-8.40 (m, 8H), 11.00-11.10 (m, 8H); $^{13}$C NMR (125 MHz, CDCl$_3$) δ 25.29, 25.40, 25.43, 25.46, 25.58, 25.61, 25.65, 25.66, 25.71, 25.82, 25.86, 26.08, 26.17, 26.20, 26.23, 26.26, 26.29, 26.35, 26.41, 28.88, 29.07, 29.59, 29.61, 29.69, 29.76, 30.28, 30.85, 32.12, 50.03, 52.47, 68.13, 70.52, 70.57, 71.03, 71.31, 72.51, 72.63, 72.95, 76.72, 76.98, 77.23, 112.26, 114.57, 118.23, 120.60, 124.42, 125.89, 128.59, 145.34, 146.54, 161.34, 163.19, 170.36; HRMS (MALDI TOF) calculated for C$_{236}$H$_{302}$N$_{40}$NaO$_{43}$ 4410.1 (M+Na)+, observed 4409.5 (average mass).

Acid Stability of Octatriazole-octaester.

Octatriazole-octaester (mg/mL) was dissolved in 1:9 THF-aqueous 2N acetic acid (pH approximately 2.2) and the solution kept at room temperature under air. Aliquots were removed at h, h, h, and 24 h, extracted with ethyl acetate (which removed all the color from the aqueous phase), and the extracts analyzed by TLC and finally by MALDI-TOF mass spectrometry. No decomposition was observed.

Octatriazole-octaacid.

Octatriazole-octaester (600 mg, 0.137 mmol) was dissolved in a mixture of THF and methanol (9:1, 75 mL), aqueous 2N LiOH (25 mL) was added, and the reaction mixture was stirred at room temperature. Progress of the reaction was monitored by TLC using 10% methanol in CH$_2$Cl$_2$ plus 0.1% ammonium hydroxide. After 24 h, the mixture was extracted with EtOAc (2×75 mL), the organic phases combined, washed with water (50 mL), brine, dried over anhydrous Na$_2$SO$_4$, filtered, and volatiles removed in vacuo to leave the product as a yellow viscous liquid (538 mg, 0.12 mmol, 90%) which was used in the next step without purification. $^1$H NMR (500 MHz, DMSO) δ 1.10-1.80 (m, 144H), 2.50-2.60 (m, 16H), 3.00-4.40 (m, 45H), 5.36 (m, 1H), 6.90-7.20 (m, 24H), 7.65-8.40 (m, 40H); $^{13}$C NMR (125 MHz, DMSO) δ 24.74, 24.81, 24.88, 25.31, 25.53, 25.58, 25.63, 25.77, 28.29, 28.51, 28.73, 28.99, 29.16, 29.21, 29.26, 29.67, 29.87, 30.25, 31.98, 33.97, 34.20, 34.70, 39.00, 39.17, 39.33, 39.50, 39.67, 39.76, 39.83, 39.92, 40.00, 43.05, 49.08, 54.88, 60.39, 65.89, 67.82, 113.75, 114.77, 114.93, 118.07, 121.33, 122.36, 124.18, 124.24, 125.15, 125.83 140.69, 128.41, 139.06, 140.61, 142.68, 144.38, 145.62, 145.84, 146.60, 148.06, 152.64, 161.02, 163.20, 171.44, 186.04; HRMS (MALDI TOF) calculated for C$_{228}$H$_{286}$N$_{40}$NaO$_{43}$ (M+Na)+4298.0, observed 4299.3 (average mass).

Octatriazole Sodium Salt

Octatriazole-octaacid from the previous section was dissolved in a mixture of acetonitrile and water (1:9) plus a few drops of DMSO and the solution loaded onto a column packed with 150 g of Dowex 50w-8x (sodium form). The column was eluted with distilled water (300 mL), the volume of the eluent reduced in vacuo to approximately 50 mL, and the solution subjected to lypholyzation to give 480 mg (0.10 mmol, 90%) of the product as a non-hygroscopic bright yellow solid, mp 74-76° C. $^1$H NMR (500 MHz, DMSO) δ 1.10-1.80 (m, 128H), 2.40-2.60 (m, 32H), 3.00-4.30 (m, 45H), 5.30 (m, 1H), 6.90-7.40 (m, 24H), 7.60-7.80 (m, 32H), 8.20-8.30 (m, 8H); HRMS (MALDI TOF) calculated for C$_{228}$H$_{286}$N$_{40}$NaO$_{43}$ (M+Na)+4298.0, observed 4298.2 (average mass).

Example II

Preparation and Use of Oral Dosage Form of Drug

In Vivo Mouse Model:

In the first study, Dextran Sulfate Sodium Salt (DSS) was added to the drinking water of the mice (male BALB/c mice, aged 8-10 weeks, n=per group) at a concentrations of 4% for a period of five days, followed by normal drinking water for seven days. Mice were given daily gastric gavage of the placebo (suspension medium Ora-Blend SF, Paddock Laboratories) or test compounds suspended in Ora-Blend SF using reusable feeding gavage needles (straight, 25 mm, 22G, 1.25 mm tip diameter, Fine Science Tools). Groups: 1) regular drinking water+placebo, 2) DSS+placebo, 3) DSS+sulfasalazine (111.5 mg/kg/day), 4) DSS+compound (155.7 mg/kg/day). Mice were measured daily for changes in weight compared to the starting weight. Upon completion of the study, the colon was harvested from each mouse. Colons were weighed and measured for length. Sulfasalazine (2) was purchased from Sigma-Aldrich. Compound was made as described in this paper. DSS was purchased from Affymetrix. In the second study, the percentage of DSS was reduced to 3% and the mice were exposed for days, followed by days with water.

Cytokine Measurement:

Mesenteric lymph nodes (MLNs) were harvested from the mice and gently disassociated using the frosted ends of sterilized glass slides to get a single cell suspension. The total cell suspension from the MLNs was then exposed to CD3/CD28 activation Dynabeads® purchased from Invitrogen using the manufacturer's protocol to stimulate proliferation of T cells and their associated cytokine production. Quantification of cytokines was measured with a multiplex panel kit from the Millipore Corporation using the manufacturer's protocol and LiquiChip (Luminex 100, Qiagen). The cytokines measured included IFN-γ, IL-17, TNF-α, IL-1β, IL-6 and MMP8 (the latter as a surrogate marker of mucosal neutrophil infiltration). Duplicates of samples were tested. MasterPlex QT software (Mirai-Bio) was used for data analysis.

The results were plotted in FIGS. 4A and 4B and 5A and 5B.

The present disclosure has been described in connection with delivery to the colon of a drug or prodrug for treating IBD, microscopic colits, and eosinophilic colitis. However, the same technology may be employed for delivery of other drugs or prodrug to the lower GI tract or other sites along the GI tract. The delivery system also may be used for colonic targeting drugs currently existing on the market or in development for the treatment of other diseases and infections of the lower GI tract including, but not limited to, colorectal cancer (prevention and treatment), colonic polyps, acute and chronic diarrheal diseases, bacterial overgrowth, diverticulitis, irritable bowel syndrome and other types of functional abdominal pain disorders. The delivery system also may be used for delivering compounds isolated from probiotics strains directly to a targeted region in the lower GI tract.

A feature and advantage of the present disclosure is that the delivery system permits delivery of 5-ASA and other drugs and prodrugs in liquid form, which permits addition of the drugs or prodrugs to beverages, ice cream or the like. The lack of commercially available oral liquid formulations poses a frequent challenge in providing medications to pediatric patients, geriatric patients, patients with feeding tubes, and patients who cannot swallow solid dosage forms. Such a formulation would be invaluable for pediatric gastroenterologists for the treatment of early onset IBD in order eliminate difficulties related to the size of delayed-release tablets/capsules, increase palatability, compliance, and ultimately, clinical efficacy.

Various features may be made in the foregoing disclosure without departing from the spirit and scope thereof.

The invention claimed is:

1. A pharmaceutical composition comprising a compound of the formula:

wherein

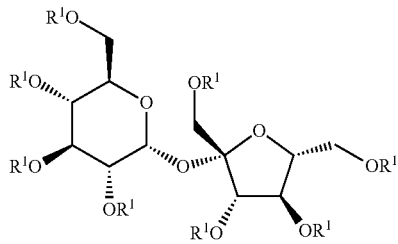

$R^1$ is a moiety of the formula:

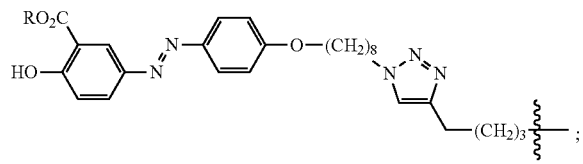

and

R is H, $CH_3$ or Na.

2. The pharmaceutical composition of claim 1, wherein R is H.

3. The pharmaceutical composition of claim 1, wherein said compound is in a solid carrier.

4. The pharmaceutical composition of claim 1, wherein said compound is in a liquid carrier.

5. A method for treating an individual for an inflammatory bowel disease comprising administering to the individual in need thereof a therapeutically effective amount of a pharmaceutical composition of claim 1.

6. The method of claim 5, wherein the inflammatory bowel disease is ulcerative colitis.

7. The method of the claim 5, wherein the inflammatory bowel disease is Crohn's Disease.

* * * * *